(12) United States Patent
Lawrenz-Stolz

(10) Patent No.: US 6,785,440 B1
(45) Date of Patent: Aug. 31, 2004

(54) ASSEMBLY FOR FOCUSING AND COUPLING THE RADIATION PRODUCED BY A SEMICONDUCTOR LASER INTO OPTICAL FIBERS

(75) Inventor: Jörg Lawrenz-Stolz, Suesel-Zarnekau (DE)

(73) Assignee: Coherent, Inc., Santa Clara, CA (US)

( * ) Notice: Subject to any disclaimer, the term of this patent is extended or adjusted under 35 U.S.C. 154(b) by 0 days.

(21) Appl. No.: 09/283,169

(22) Filed: Apr. 1, 1999

Related U.S. Application Data

(62) Division of application No. 08/982,018, filed on Dec. 1, 1997, now Pat. No. 5,949,932, which is a continuation of application No. 08/047,421, filed on Apr. 15, 1993, now abandoned.

(30) Foreign Application Priority Data

Apr. 16, 1992 (DE) .......................................... 42 12 832
Nov. 13, 1992 (DE) .......................................... 42 38 434

(51) Int. Cl.⁷ ............................................... G02B 6/32
(52) U.S. Cl. ............................ 385/33; 385/34; 385/89; 385/93
(58) Field of Search .......................... 385/31–35, 88–94, 385/49; 372/75, 101

(56) References Cited

U.S. PATENT DOCUMENTS

| | | | |
|---|---|---|---|
| 3,894,789 A | 7/1975 | Kobayashi et al. | ........ 350/96 C |
| 4,079,404 A | 3/1978 | Comerford et al. | ........... 357/19 |
| 4,147,403 A | 4/1979 | d'Auria et al. | ........... 350/96.18 |
| 4,193,663 A | 3/1980 | Timmermann | ........... 350/96.18 |
| 4,269,648 A * | 5/1981 | Dakss et al. | .................. 385/35 |
| 4,440,470 A | 4/1984 | Khoe | ........................ 350/96.2 |
| 4,456,330 A | 6/1984 | Blüdau | ..................... 350/96.18 |
| 4,490,020 A | 12/1984 | Sakaguchi et al. | ....... 350/96.18 |
| 4,687,285 A | 8/1987 | Hily et al. | ................ 350/96.18 |
| 4,701,011 A | 10/1987 | Emkey et al. | ........... 350/96.18 |

(List continued on next page.)

FOREIGN PATENT DOCUMENTS

JP     1-271711     10/1989     ............ G02B/6/32

OTHER PUBLICATIONS

M. Maeda, I. Ikushima, K. Nagano, M. Tanaka, H. Nakashima & R. Itoh, "Hybrid laser–to–fiber coupler with a cylindrical lens," *Applied Optics*, Jul. 1977, vol. 16, No. 7, pp. 1966–1970.

J.D. Crow, L.D. Comerford, J.S. Harper, M.J. Brady & R.A. Laff, "Gallium arsenide laser–array–on–silicon package," *Applied Optics*, Feb. 1, 1978, vol. 17, No. 3, pp. 479–485.

(List continued on next page.)

*Primary Examiner*—Hemang Sanghavi
(74) *Attorney, Agent, or Firm*—Stallman & Pollock LLP

(57) ABSTRACT

An assembly for focusing and coupling radiation produced by a semiconductor laser into an optical fiber, in particular a multimode optical fiber, including a radiation-focusing element in the form of cylinder lens disposed in the area between the radiating surface of the semiconductor laser and light entrance side of the optical fiber, the length of the cylinder lens being at least equal to a width of a beam exit window defining the radiation surface of the semiconductor laser, and the diameter of the cylinder lens being substantially on the order of magnitude of the core diameter of the optical fiber. The cylinder lens is in the form of glass fiber lens directly glued onto, fused with, or melted onto the light entrance side of the optical fiber which extends substantially at right angles to the orientation of the cylinder lens. The assembly can be used in particular to produce high-powered laser modules up to 50 watts and are very suitable as pumping laser for an end-pumped solid state laser, for example for medical applications or for materials processing.

12 Claims, 2 Drawing Sheets

U.S. PATENT DOCUMENTS

| | | | | |
|---|---|---|---|---|
| 4,744,620 | A | 5/1988 | Ueno et al. | 350/96.18 |
| 4,785,459 | A | 11/1988 | Baer | 372/75 |
| 4,818,062 | A | 4/1989 | Scifres et al. | 350/96.29 |
| 4,830,453 | A | 5/1989 | Khoe | 350/96.18 |
| 4,837,771 | A | 6/1989 | Baer | 372/75 |
| 4,894,839 | A | 1/1990 | Baer | 372/93 |
| 5,007,700 | A * | 4/1991 | Albares | 385/38 |
| 5,016,964 | A | 5/1991 | Donnelly | 350/96.18 |
| 5,121,457 | A | 6/1992 | Foley et al. | 385/89 |
| 5,127,068 | A | 6/1992 | Baer et al. | 385/34 |
| 5,163,108 | A | 11/1992 | Armiento et al. | 385/89 |
| 5,202,893 | A | 4/1993 | Kubota et al. | 372/34 |
| 5,268,978 | A | 12/1993 | Po et al. | 385/33 |
| 5,343,548 | A * | 8/1994 | Hall et al. | 385/89 |
| 5,436,990 | A | 7/1995 | Head et al. | 385/34 |
| 5,579,422 | A | 11/1996 | Head et al. | 385/34 |
| 5,629,997 | A | 5/1997 | Hardy, Jr. | 385/33 |

OTHER PUBLICATIONS

Yu. Kh. Ayunts, M.I. Belovolov, E.M. Dianov & A.B. Tsibulya, "Coupling of optical radiation into fiber waveguides of elliptic cross section," *Sov. J. Quantum Electron.*, vol. 13, No. 12, Dec. 1983, pp. 1584–1590.

V.A. Dombrovskii, S.A. Dombrovskii, E.F. Pen, A.N. Potapov & Z.L. Pustovaya, "Coupling a Visible–Range Semiconductor Laser with a Single–Mode Optical Fiber," *Optoelectronics Instrumentation and Data Processing*, No. 3, 1990, pp. 8–14.

W. Nakwaski, "Sprzezenie lasera zlqczowego ze szklanym wloknem swiatlowodowym," *Przeglad Telekomunikacyjny*, Oct. 1980, pp. 341–344.

M. Saruwatari & K. Nawata, "Semiconductor laser to single–mode fiber coupler," *Applied Optics*, vol. 18, No. 11, Jun. 1, 1979, pp. 1847–1856.

E. Weidel, "Light coupling problems for GaAs laser–multimode fibre coupling," *Optical and Quantum Electronics*, No. 8, 1976, pp. 301–307.

D. Crow, J.S. Harper, L.D. Comerford, M.J. Brady & R.A. Laff, "GaAs Laser Source Package for Multichannel Optical Links," Topical Meeting on Optical Fiber Transmission, *Digest of Technical Papers (Opt. Soc. Am)*, 1977, pp. WB6/1–3.

E. Weidel, "New Coupling Method for GaAs–Laser–Fibre Coupling," *Electronic Letters*, vol. 11, No. 18, Sep. 1975, pp. 436–437.

S. Maslowski & O. Krumpholz, "Sender–und Koppeltechnik für Lichtleitfasersysteme," *Flektroniker*, No. 11, 1976, pp. EL32–EL34. (Translation Included).

L.D. Comerford & J.D. Crow, "Synchronized Output Laser Array." *IBM Technical Disclosure Bulletin*, vol. 20, No. 4, Sep. 1977, pp. 1638–1639.

E.A. Cunningham, "Collimated Light Source with Laser Diode and Microcylinderical Lens," *IBM Technical Disclosure Bulletin*, vol. 19, No. 2, Jul. 1976.

R.B. Allen & S.J. Scalise, "Continuous Operation of a YAIG:Nd Laser by Injection Luminescent Pumping," *Applied Physics Letters*, vol. 14, No. 6, Mar. 15, 1969, pp. 188–190.

* cited by examiner

ASSEMBLY FOR FOCUSING AND COUPLING THE RADIATION PRODUCED BY A SEMICONDUCTOR LASER INTO OPTICAL FIBERS

CROSS REFERENCE TO PRIOR APPLICATIONS

This application is a division of application Ser. No. 08/982,018, filed Dec. 1, 1997, now U.S. Pat. No. 5,949,932, which is a Continuation of application Ser. No. 08/047,421, filed Apr. 15, 1993 now abandoned.

TECHNICAL FIELD OF THE INVENTION

The present invention relates to an assembly for focusing and coupling the radiation produced by a semiconductor laser diode) into an optical fiber, in particular a multimode optical fiber, with a radiation-focusing element in the form of a cylinder lens being disposed in the area between a radiating surface of the laser and a light entrance side of the optical fiber, the cylinder lens being oriented substantially parallel to the multimode direction of the radiating surface of the semiconductor laser. The invention also relates to a laser module having a plurality of assemblies of the type defined above.

Finally the invention relates to an assembly for focusing and coupling the emissions produced by a semiconductor laser array (laser diode array) or a two-dimensional semiconductor laser structure (laser diode stack) into a corresponding number of individual optical fibers, in particular multimode optical fibers, with an optical system for focusing radiation being provided in the area between the radiating surface of the laser diode array or stack and the individual light entrance sides of the optical fibers.

DESCRIPTION OF BACKGROUND ART

The source "Applied Optics", Vol. 16, no. 7, Jul. 1977, pp. 1966–1970, discloses an assembly having the features described in paragraph 1 of the "Technical field of the invention" above. This source (see in FIG. 5 on p. 1968) describes a specially designed carrier element for coupling a semiconductor laser, e.g. a GaAs diode, and an optical fiber having a circular cross section, said element simultaneously carrying the cylinder lens for coupling the laser radiation produced by the GaAs diode into the subsequent optical fiber. This substantially cylindrical carrier element is provided on the top with a given number of V-groove recesses which are preshaped by mechanical, i.e. metal-removing, processing of the carrier element material, e.g. copper, in accordance with the intended coupling between laser, cylinder lens and optical fiber and in order to guarantee the necessary optical adjustment of these elements to one other. Due to this design of the carrier element the optical elements subsequent to the GaAs diode, i.e. the cylinder lens and the optical fiber, can be inserted into these above-mentioned recesses, the mutual adjustment of these elements being dependent on the precision with which the corresponding recesses have been machined in the carrier element. Very low tolerances are of course permissible here to allow for the necessary ultimate adjustment.

The mechanical requirements for the tolerances of such a carrier element, and in particular the required positioning accuracy for the GaAs diode relative to the subsequent optical elements, are thus extremely high since particularly this laser diode must be applied and fastened to the surface of the carrier element, for example by gluing or soldering. This means that the production and processing of such a carrier element is very elaborate to permit the necessarily very low tolerances to be met.

This known assembly is intended to focus as much as possible of the radiation emitted by one semiconductor diode into the core of the optical fiber, e.g. a multimode fiber with a circular cross section. There is no intention here to provide a laser module with the greatest possible power and radiation quality.

Further, "Applied Optics", Vol. 17, No. 3, 1978, p. 479 ff., discloses an assembly wherein each individual laser of a monolithic laser diode array is coupled by means of a common cylinder lens to a great number of individual optical fibers. A carrier element in the form of a silicon substrate is likewise used here, a given number of V-shaped recesses being preshaped in this silicon substrate in accordance with the intended arrangement of cylinder lens and optical fibers for coupling between a laser diode and an optical fiber as in the known coupling assembly explained above.

Extremely low process tolerances are also permissible in this case. In addition, the direct contact between cylinder lens and laser diode array can drastically change the properties of the individual laser diodes, i.e. the laser diodes can very easily be mechanically destroyed when the cylinder lens is inserted into the V-shaped groove provided in the silicon substrate. In this latter assembly the manufacturing expenditure is therefore likewise considerable.

SUMMARY OF THE INVENTION

In view of the prior art described above the present invention is therefore based on the problem of providing an improved assembly for focusing and coupling the radiation produced by a semiconductor laser into an optical fiber, in particular a multimode optical fiber, primarily with the goal of realizing a highly efficient coupling between a multimode high-power laser diode and a multimode optical fiber. The invention is also based on the problem of providing a laser module, in particular a pumping module, with much greater power and maximum radiation quality as compared with known laser diode modules.

Finally there is also the requirement that assemblies utilizing the above-described type of coupling should be able to be produced in a much simpler and less expensive way compared with the prior art explained above, while ensuring all requirements for the precision of adjustment. The first mentioned problem is solved according to the invention by adapting a cylinder lens of the above-mentioned type to have a substantially equal to the width of a beam exit window defining the radiating surface of the semiconductor laser and whose diameter is substantially on the order of magnitude of the core diameter of the optical fiber, and preferably smaller than this core diameter, and by directly gluing the lens to, fusing the lens with or melting the lens onto the light entrance side of the optical fiber extending substantially at right angles to the orientation of the cylinder lens.

Further, the present invention makes it possible to obtain a laser module with high power and high radiation quality while having a small numerical aperture. A given number of individual assemblies designed according to the present invention are united into a module, the corresponding individual optical fibers being bunched such that the free ends, i.e. the light exit sides, of all optical fibers are disposed in a configuration that can be selected or predetermined at will.

A laser module of the type characterized above can be used in preferred fashion as a pumping laser for systems with pumped solid state lasers, the total laser radiation obtained on the light exit sides of the bunched optical fibers serving as the pumping energy for the subsequent pumped laser.

Such optical pumping (longitudinal and transversal) can be performed for example with or without frequency multiplication, for example for pumping a neodymium-YAG laser. It is also possible to use a laser module of the type characterized above as a laser particularly for medical applications or for materials processing. In such cases, the total laser radiation obtained on the light exit sides of the bunched optical fibers is utilized as the energy for the particular medical treatment process or the particular materials processing operation.

Furthermore the light exit sides of the bunched optical fibers can preferably be combined in a matrix-shaped assembly or a linear assembly. According to yet another feature of the invention any desired symbols can be applied in matrix form to an object as "laser marking" by a preferably selective and individual drive of the individual diode lasers and imaging on the object. In a corresponding way, machining places can be preselected in matrix form strictly by the electric drive of the individual diode lasers, which provides special advantages in particular for micromachining, e.g. when soldering, welding or drilling.

A further possibility of designing a laser module within the scope of the present invention is to couple and combine the radiating surfaces of laser diode arrays or of two-dimensional structures, so-called laser diode stacks, into corresponding optical fibers, instead of using individual assemblies of the type explained above each having individual laser diodes.

In an assembly for focusing and coupling the emissions produced by a semiconductor laser array or a two-dimensional semiconductor laser structure into a corresponding number of individual optical fibers according to the features of yet another embodiment of the invention, the optical system for focusing radiation is formed by a cylinder lens dimensioned in accordance with the number and arrangement of the individual optical fibers and oriented substantially parallel to the multimode directions of radiation of each laser diode.

The length of the lens is adapted substantially to the total width of the beam exit windows defining the radiating surface of the laser diodes and its diameter is substantially on the order of magnitude of and preferably smaller than the core diameter of the particular individual optical fiber. The cylinder lens is directly glued to, fused with or melted onto all associated light entrance sides of the optical fibers extending substantially perpendicular to the orientation of the cylinder lens.

According to further advantageous embodiments of the assembly, if semiconductor laser arrays are used, the individual cylinder lens is preferably formed as a glass fiber lens. The same applies if two-dimensional semiconductor laser stacks are used. The additional advantage of such semiconductor laser arrays or stacks is their high-precision production and the related low positional tolerance of the radiating surfaces of the corresponding semiconductor lasers or laser diodes.

A relatively small air gap may preferably be provided between the laser diode array or stack and the assembly of the cylinder lens of the optical system for focusing radiation, regarded in the directions of radiation. This avoids mutual mechanical influence between the cylinder lens and the accordingly associated laser diodes, with the advantage that neither the properties of these laser diodes are changed nor is there a danger of the laser diodes being mechanically destroyed.

The invention furthermore includes the very advantageous possibility of coupling the laser diode array or stack to the associated number of individual optical fiber-cylinder lens units by providing a holding means common to all these units. Using standard techniques (etching, CNC milling and the like) one can produce structures for such holding means in a very simple and inexpensive way with a tolerance in the micrometer range sufficient for the desired coupling of the laser diode arrays or stacks to the corresponding number of optical fibers.

If the cylinder lens is glued on for example with the aid of an epoxy adhesive, one additionally obtains the special advantage that this adhesive centers the cylinder lens or fiber lens itself on the light entrance sides of the individual optical fibers. A further advantage of the direct gluing method is obtained by using an epoxy adhesive that is very thin and has very low absorption at the laser wavelength of approximately 810 nm emitted by the laser diodes for example. Excess adhesive tends to increase the coupling efficiency even further.

On the basis of first experiences it can be said that a coupling efficiency of about 70% is typically obtainable, but a coupling efficiency up to almost 100% is also theoretically possible.

If a semiconductor laser array (laser diode array) or a two-dimensional semiconductor laser structure (laser diode stack) is provided in an assembly according to the present invention this assembly can also be used as a pumping laser for systems with pumped solid state lasers, the total laser radiation available on the light exit sides of the preferably bunched optical fibers serving as the pumping energy for a subsequent pumped laser.

It is especially advantageous to bunch all individual optical fibers of the corresponding semiconductor laser array or the corresponding two-dimensional semiconductor laser stack in such a way that the free ends, i.e. the light exit sides, of these optical fibers are disposed in configurations that can be selected or predetermined at will.

For example, a configuration can be provided such that the free ends (light exit sides) of the optical fibers are combined in a geometrically closest packing.

Furthermore, a configuration can be selected such that the free ends (light exit sides) of all optical fibers form a substantially rectangular matrix. On the other hand, a configuration is also possible such that the free ends (light exit sides) of all optical fibers form a line.

Finally, it is also possible to drive the individual laser diodes selectively and individually so that the radiation emerges from a corresponding selection of light exit sides of the optical fibers, allowing the production of beam exit patterns that can be selected or predetermined at will. Using such an assembly one can for example mark an object with a pattern representing whole letters, numbers or other symbols in matrix form or representing parts of letters, numbers or other symbols so that several matching parts result side by side in whole letters, numbers or other symbols in matrix form.

The ends of the combined fibers can be imaged on a given place on an object (the image plane) either directly, if the distance to the image plane is small relative to the total diameter of the fiber bundle, or with the aid of an optical system, so that the laser light of the luminous fiber ends produces on the surface of this object a change which causes the desired marking of the object.

There are a number of preferred possibilities of application for the inventively designed assembly. For example, one such application is to use the assembly as a pumping laser for systems with pumped solid state lasers, the laser radiation obtained on a light exit side of the optical fiber serving as the pumping energy for the subsequent pumped laser.

The possibility of use described above also exists, for example, when, a given number of assemblies according to any of the embodiments are united into a module, the corresponding optical fibers of these individual assemblies being combined such that the free ends (light exit sides) of all optical fibers are disposed in a configuration that can be selected or predetermined at will. Furthermore, an inventively designed assembly or a corresponding laser module can be preferably used for tissue removal, coagulation, heat treatment, stimulation or other optical treatments in the medical field, or for materials processing, the laser radiation obtained on the light exit side of the assembly or the laser module serving to produce the above-mentioned effects.

If an inventive assembly or an inventive laser module is used for flexible materials processing or for tissue treatment it is also possible for the ends of the combined fibers to be imaged on a given place on a workpiece or tissue (i.e. the image plane) either directly, if the distance to the image plane is small relative to the total diameter of the fiber bundle, or with the aid of an optical system, the desired materials processing or tissue treatment then occurring at this place.

BRIEF DESCRIPTION OF THE DRAWINGS

The invention shall be explained in more detail in the following with reference to embodiment examples and to the enclosed drawings, in which.

DETAILED DESCRIPTION OF PREFERRED EMBODIMENTS

Figure 1:
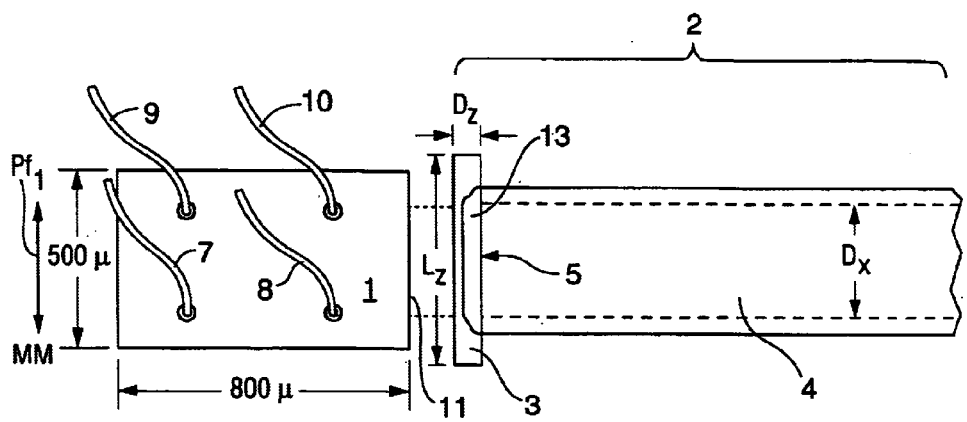
FIG. 1 shows schematically a top view of a preferred assembly for focusing and coupling the radiation produced by a laser diode into a multimode optical fiber with a circular cross section.

FIG. 1 shows a schematic top view of an assembly provided with a multimode optical fiber 4 having a circular cross section for focusing and coupling the radiation produced by a laser diode 1 in the form of a chip. The diameter of the fiber core of optical fiber 4 is for example 200 micrometers. The dimensions of the chip forming laser diode 1 are for example 800 micrometers in length and 500 micrometers in width. This is preferably a so-called high-power laser diode with a beam exit window 11 whose area is for example 200 micrometers by 0.5 micrometers. The width of beam exit window 11 can also vary within a range between 50 and 500 micrometers, and the radiating surface can also consist of many small, closely packed individual emitters. Beam exit window 11 of laser diode 1 emits a multimode laser beam with a typical aperture angle of 10 to 12°. This corresponds to a numerical aperture of about 0.1. The direction of a multimode laser beam extends in the wide direction of laser diode 1, this multimode direction of laser diode 1 being indicated in FIG. 1 by arrow $Pf_1$.

However, in the very small height of beam exit window 11 (0.5 micrometers) laser diode 1 radiates in the basic mode ($TEM_{00}$) at an angle of 400 to 600 corresponding to the height of the luminous area, corresponding to a numerical aperture of about 0.4. FIG. 1 also denotes the electric leads to laser diode 1 by reference numbers 7, 8, 9 and 10.

Multimode optical fiber 4 which is circular in the preferred embodiment is disposed so that its light entrance side 5 is spaced opposite beam exit window 11 of laser diode 1, light entrance side 5 being oriented substantially parallel to the multimode direction according to arrow $Pf_1$, of the radiating surface of laser diode 1.

Figure 2:
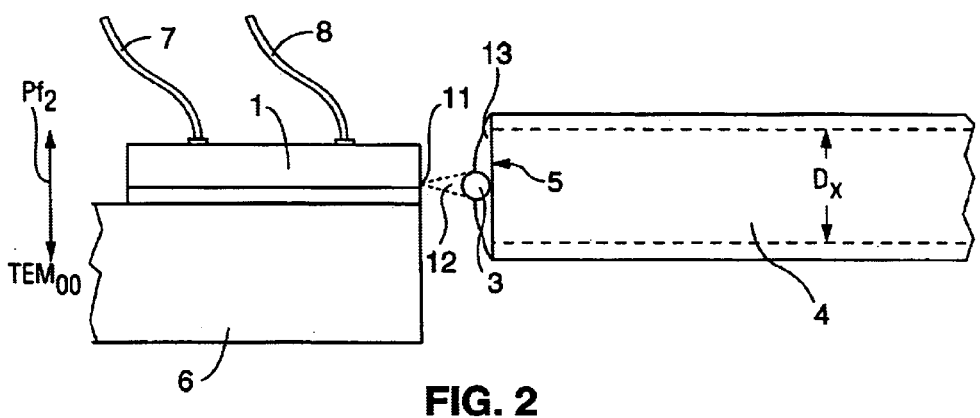
FIG. 2 is a schematic side view of the assembly according to FIG. 1.

Light entrance side 5 of multimode optical fiber 4 is also provided with a radiation-focusing element in the form of a cylinder lens 3 which is glued directly to light entrance side 5 by means of an epoxy adhesive 13 (cf. FIG. 2).

Cylinder lens 3 is thus likewise oriented substantially parallel to the multimode direction according to arrow $Pf_1$, of the radiating surface of light exit window 11 of laser diode 1. Length $L_z$ of cylinder lens 3 is adapted substantially to the width of beam exit window 11 defining the radiating surface of laser diode 1. In any case, length $L_z$ of cylinder lens 3 should not be smaller than the width of beam exit window 11, and $L_z$ will generally be somewhat greater than the width of beam exit window 11 in the multimode direction.

FIG. 2 shows a schematic side view of the assembly according to FIG. 1. The $TEM_{00}$ direction of laser diode 1 is indicated here by arrow $Pf_2$. The angle of radiation of the $TEM_{00}$ direction of laser diode 1 is denoted as 12, the numerical aperture being e.g. 0.4 as already mentioned. Diameter $D_z$ of cylinder lens 3 is generally selected so as to be in the order of magnitude of core diameter $D_x$ of optical fiber 4.

In the preferred embodiment explained here, however, diameter $D_z$ of cylinder lens 3 is selected in a range between 80 and 100 micrometers and is thus below core diameter $D_x$=200 micrometers of optical fiber 4. If optical fibers with a circular cross section are used, diameter $D_z$ of cylinder lens 3 will preferably be smaller than core diameter $D_x$ of optical fiber 4.

Cylinder lens 3 glued directly to light entrance side 5 of optical fiber 4 makes it possible for virtually the total light of laser diode 1 to be focused into the core of optical fiber 4. This is virtually an imaging of the $TEM_{00}$ direction of laser diode 1 onto light entrance side 5 of multimode optical fiber 4 with the aid of the optical properties of cylinder lens 3.

The size and numerical aperture of optical fiber 4 are preferably selected so as to correspond to the width and the angle of radiation or the numerical aperture in the multimode direction of laser diode 1. The epoxy adhesive used by way of example for gluing cylinder lens 3 to light entrance side 5 of optical fiber 4, is very thin and has a comparatively low absorption at the laser wavelength of e.g. 810 nm produced here.

As has been shown in practice, excess adhesive tends to increase the coupling efficiency between laser diode 1 and optical fiber 4 even further. The obtained coupling efficiency is for example 70%.

For cylinder lens 3 one can preferably use a fiber lens which in the simplest case consists of a piece of customary glass fiber. However there are also fiber lenses on the market which are especially intended for imaging laser diodes and are likewise well suited as cylinder lenses in the case of the present invention. Instead of gluing cylinder lens 3, for example a fiber lens, directly onto light entrance side 5 of optical fiber 4 one can also melt cylinder lens 3 directly onto optical fiber 4, this being done for example with the aid of a $CO_2$ laser or an arc or the like.

Figure 3:
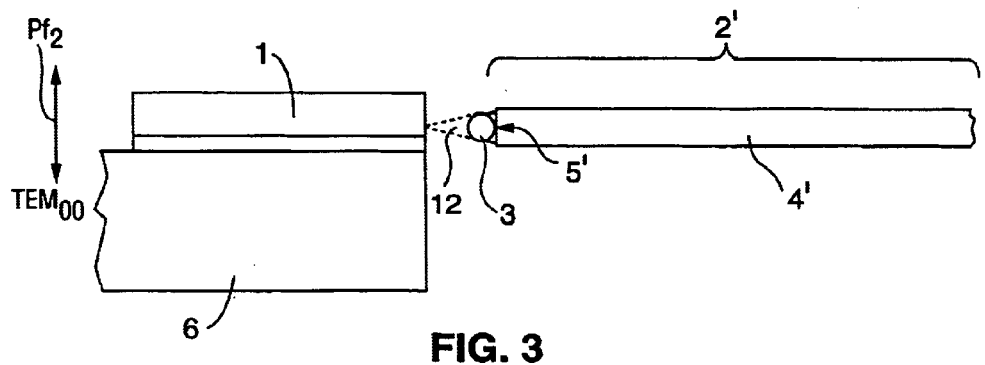
FIG. 3 is a schematic side view of a second preferred embodiment of an assembly for focusing and coupling the radiation produced by a laser diode into a multimode optical fiber which in this case has a rectangular cross section.

Such melting is useful in particular when the multimode optical fiber is a fiber with a substantially rectangular cross section, as is explained in more detail with reference to FIG. 3. FIG. 3 is a side view corresponding to FIG. 2 of an assembly for focusing and coupling the radiation produced by a laser diode 1 into a multimode optical fiber 4' which has a rectangular cross section and the dimensions of for example 200 micrometers in width and 20 micrometers in height. A cylinder lens or fiber lens 3 is again glued directly to light entrance side 5 of multimode optical fiber 4, cylinder lens 3 in this case having a diameter of for example 20 micrometers, corresponding to the height of rectangular optical fiber 4'. However diameters of cylinder lens 3 in the order of magnitude of 5 to 10 micrometers are also conceivable, i.e. in the order of magnitude of the diameter of a single mode optical fiber.

As is also apparent from FIGS. 2 and 3, laser diode 1, e.g. a GaAs diode, is disposed on a carrier element 6, e.g. a silicon substrate.

As already explained in detail with reference to FIGS. 1 to 3, the principle of coupling involves the inventive assembly in direct gluing or fusion of a cylinder lens with the beam entrance side of an optical fiber which extends substantially at right angles to the orientation of this cylinder lens. This results in a virtually firm compound between the cylinder lens or fiber lens and the optical fiber, at the same time achieving a preadjustment since the cylinder or fiber lenses are centered quasi automatically on the optical fibers.

Consequently, prefabricated units including cylinder lenses and optical fibers, for example, can be kept in stock, while for practical application in connection with a laser diode the unit need only be centered with respect to the diode but otherwise no further adjustment measures performed with respect to the coupling unit itself.

As noted above, FIG. 1 denotes such an optical coupling unit including an optical fiber 4 with a circular cross section and a cylinder lens 3 glued on its face by adhesive 13, while FIG. 3 depicts another such optical coupling unit including an optical fiber 4' with a rectangular cross section and a cylinder lens 3 glued to its face.

Furthermore FIGS. 1 to 3 also indicate that a comparatively small air gap is provided in each case between beam exit window 11 of laser diode 1 and cylinder lens 3, regarded in the particular directions of radiation, so that an impairment of the properties of the laser diode or mechanical damage to it or even destruction of it can be avoided from the beginning. In the embodiment according to FIG. 3 one can use a substantially flat, round optical fiber instead of an optical fiber with a rectangular cross section.

Figure 5:
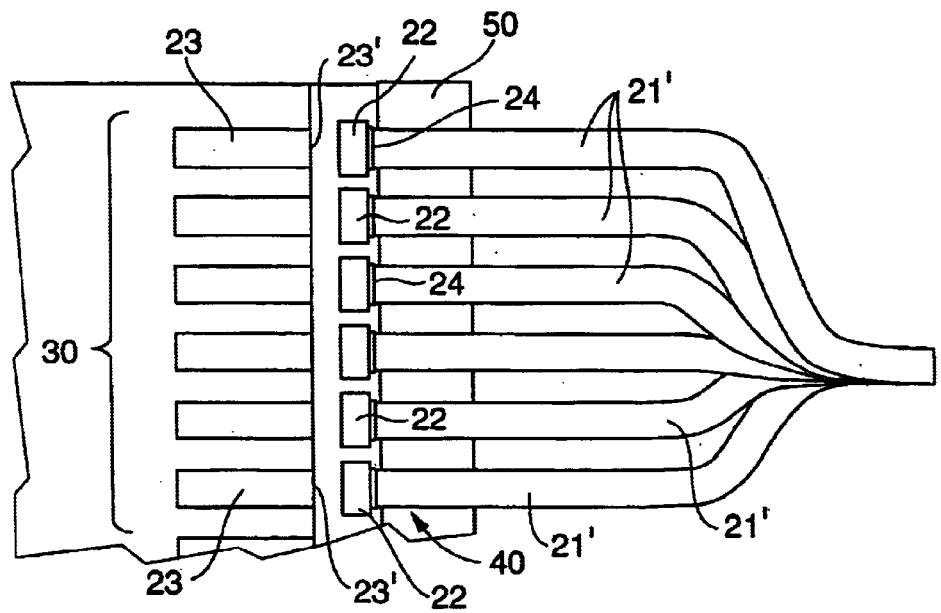
FIG. 5 shows a another preferred embodiment of an assembly for focusing and coupling the emissions produced by a laser diode array into a corresponding number of individual optical fibers which in this case have a rectangular cross section (showing a schematic top view of this assembly)
Figure 6:
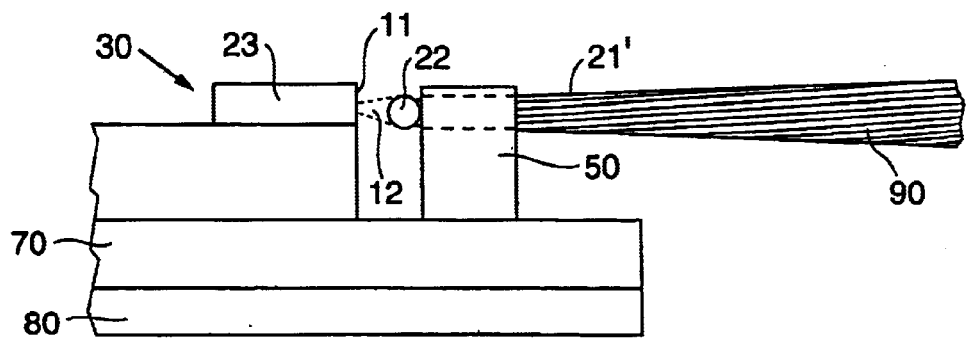
FIG. 6 shows a schematic side view of the assembly according to FIG. 5.

FIGS. 5 and 6 show an embodiment example of a laser module provided with a group of several multimode high-power laser diodes 23 disposed side by side, i.e. virtually a laser diode array 30, the emissions produced by individual laser diodes 23 being coupled into a corresponding number of individual multimode optical fibers with a rectangular cross section.

As in the assemblies according to FIGS. 1, 2 and 3 an optical system for focusing radiation is disposed here in the area between the radiating surface of laser diode array 30 and individual light entrance sides 24 of the particular associated optical fiber 21 with a rectangular cross section. In the present embodiment example this optical system is formed by a number of assemblies of individual cylinder lenses 22 corresponding to the number and arrangement of individual optical fibers 21'.

All cylinder lenses 22 are oriented substantially parallel to the multimode direction of radiation of each laser diode 23 of laser diode array 30; also, length Lz of each cylinder lens 22 is adapted substantially to the width of a beam exit window 23' defining the radiating surface of particular laser diode 23, while diameter $D_z$ of cylinder lenses 22 is substantially equal to the height of each individual optical fiber 21' having a rectangular cross section.

Each individual cylinder lens 22 is glued directly onto the associated light entrance side 24 of optical fibers 21' in the same way as already explained above with reference to FIGS. 1 to 3. One thus again obtains optical coupling units each comprising cylinder lens 22 and optical fiber 21', which are denoted in FIG. 5 by reference number 40.

Furthermore, FIGS. 5 and 6 show that a holding means 50 is provided for coupling laser diode array 30 to the associated number of individual optical coupling units 40 including cylinder lenses and optical fibers, the holding means holding each of individual optical fibers 21' in an initially parallel side-by-side configuration. When such an assembly is mounted, laser diode array 30 and holding means 50 are adjusted relative to each other and then fastened to a common carrier 70 shown in FIG. 6, for example by screwing or gluing.

This carrier 70 is finally disposed on a Peltier element 80. To adjust the desired laser wavelength the common carrier is tempered, the tempering additionally contributing to stabilizing the coupling. In the embodiment of FIGS. 5 and 6 relatively small air gaps are also provided in each case between laser diode array 30 and the assembly of individual cylinder lenses 22, regarded in the directions of radiation.

It is of special importance for the assembly illustrated in FIGS. 5 and 6 that all optical fibers 21' can be bunched so that their free ends, i.e. their light exit sides, are disposed in a configuration that can be selected or predetermined at will, and in particular, combined in a geometrically close packing. In practice this means that individual laser diodes 23 in laser diode array 30 can be coupled into a very high-power laser module by first coupling laser diode array 30 to optical fibers 21' having a rectangular cross section and then stacking the fibers on the light exit side into a preferably square bundle 90, for example a bundle with edge lengths of 220 micrometers by 220 micrometers and a numerical aperture of 0.11.

Figure 4:
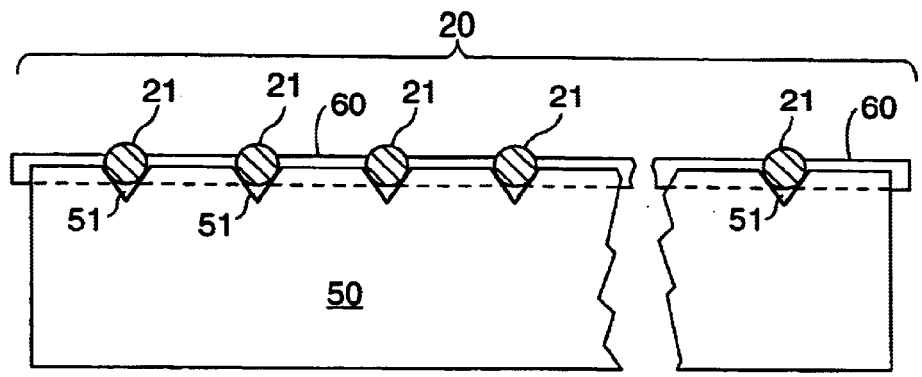
FIG. 4 shows schematically a sectional view through a preferred assembly for focusing and coupling the emissions produced by a number of laser diodes disposed in a group, i.e. a so-called laser diode array, into a corresponding number of individual optical fibers with a circular cross section.

Finally, FIG. 4 shows an example of the preferred embodiment of an assembly for focusing and coupling the emissions produced by a semiconductor laser array into a corresponding number of individual multimode optical fibers 21, in which one uninterrupted cylinder lens 60 is provided in the area between the radiating surface of the laser diode array (located behind the paper plane in FIG. 4) and the individual light entrance sides of optical fibers 21.

Cylinder lens 60 is formed for example by an appropriately long piece of a fiber lens which is dimensioned such that its length is adapted substantially to the sum of the widths of the particular beam exit windows defining the radiating surfaces of all laser diodes of the array, the diameter of cylinder lens 60 preferably being smaller than the particular core diameter of each optical fiber 21, as in the embodiment of FIG. 1. Common cylinder lens 60 is again glued onto, fused with or melted onto all light entrance sides of optical fibers 21 extending substantially perpendicular to the orientation of cylinder lens 60.

Optical fibers 21 located side by side in parallel are again held by a holding means 50 which has corresponding V-shaped grooves 51 on the top for insertion of optical fibers 21. This holding means 50 is then adjusted to the associated laser diode array, in the way already explained with reference to FIG. 6, 50 that this adjusted assembly can in turn be fastened to a common carrier as shown in FIG. 6.

In the embodiment shown in FIG. 4 the light exit sides of optical fibers 21 with a round cross section can then be combined into a bundle. For example, twelve free optical fiber ends are combined into a bundle with a diameter of about 900 micrometers, a numerical aperture of 0.11 and an output power of about 7 W.

On the basis of the assemblies shown for example in FIGS. 4, 5 and 6 one can produce high-power laser modules (up to 50 W) which are very suitable as pumping lasers for end-pumped solid state lasers, to be applied for example in medicine or for soldering or the like.

What is claimed is:

1. A laser module comprising:

a carrier element;

a laser diode assembly including a linear array of laser diodes, said laser diode assembly being mounted on the carrier element;

a holder for supporting an array of optical fibers, said holder being mounted on said carrier element spaced from the laser diode assembly to define a gap therebetween and positioned so that the light entrance sides of the fibers are aligned with laser diodes of the laser diode assembly; and an elongated cylindrical lens positioned entirely in the gap between the holder and the diode laser assembly and spaced from said diode laser assembly, said lens being attached to the light entrance sides of the optical fibers, said lens for receiving radiation emitted from the laser diodes and focusing said received radiation into the associated optical fibers.

2. A laser module as recited in claim 1, wherein said cylindrical lens is defined by an optical fiber.

3. A laser module as recited in claim 1, wherein the carrier is mounted on a Peltier element.

4. A laser module as recited in claim 1, said lens being attached to the light entrance sides of the optical fibers using a bead of glue.

5. A laser module as recited in claim 1, wherein said optical fibers are multimode optical fibers.

6. A laser module as recited in claim 1, wherein the diameter of the cylindrical lens is less than the core diameter of the optical fibers.

7. A laser module comprising:

a carrier element;

a laser diode assembly including a linear array of laser diodes, said laser diode assembly being mounted on the carrier element;

a holder for supporting an array of optical fibers, said holder being mounted on said carrier element spaced from the laser diode assembly to define a gap therebetween and positioned so that the light entrance sides of the fibers are aligned with laser diodes of the laser diode assembly; and an elongated cylindrical lens positioned entirely in the gap between the holder and the diode laser assembly and spaced from said diode laser assembly, said lens being attached to the light entrance sides of the optical fibers using a bead of glue in a manner to self center and align the cylindrical lens with respect to the light entrance sides, said lens for receiving radiation emitted from the laser diodes and focusing said received radiation into the associated optical fibers.

8. A laser module as recited in claim 7, wherein said cylindrical lens is defined by an optical fiber.

9. A laser module as recited in claim 7, wherein the carrier is mounted on a Peltier element.

10. A laser module as recited in claim 7, wherein said bead of glue is an epoxy adhesive.

11. A laser module as recited in claim 7, wherein said optical fibers are multimode optical fibers.

12. A laser module as recited in claim 7, wherein the diameter of the cylindrical lens is less than the core diameter of the optical fibers.

* * * * *